United States Patent [19]

von Fraunberg

[11] 4,002,684
[45] Jan. 11, 1977

[54] MANUFACTURE OF γ,δ-UNSATURATED KETONES

[75] Inventor: Karl von Fraunberg, Bobenheim, Germany

[73] Assignee: BASF Aktiengesellschaft, Ludwigshafen (Rhine), Germany

[22] Filed: June 26, 1975

[21] Appl. No.: 590,405

[30] Foreign Application Priority Data

July 5, 1974 Germany ........................... 2432232

[52] U.S. Cl. ..................... 260/593 R; 260/586 C; 260/638 G
[51] Int. Cl.² ........:.............................. C07C 45/00
[58] Field of Search .................... 260/593 R, 586 C

[56] References Cited
OTHER PUBLICATIONS

Naf et al., Helvetica Chemica Acta, vol. 54, pp. 1939–1949 (1971).
Parham et al., J. Org. Chem., vol. 34, No. 6, pp. 1899–1904 (1969).
Hause et al., J. Org. Chem., vol. 31, pp. 3128–3141 (1966).
Kharasch et al., J.A.C.S., vol. 63, pp. 2308–2316 (1941).
Hooz et al., Can. J. Chem., vol. 48, pp. 1626–1630 (1970).

Primary Examiner—James O. Thomas, Jr.
Assistant Examiner—James H. Reamer
Attorney, Agent, or Firm—Johnston, Keil, Thompson & Shurtleff

[57] ABSTRACT

γ,δ-Unsaturated non-cyclic aliphatic ketones are prepared by reacting specific α,β-unsaturated ketones with vinylmagnesium halide in the presence of inorganic copper compounds at temperatures below 0° C. The reaction products are valuable intermediates in the synthesis of a number of perfumes. For example, the compound 3,3-dimethyl-1-hexen-5-one which may be prepared from mesityl oxide and vinylmagnesium chloride is an intermediate for lavandulyl compounds such as lavandulol and lavandulyl acetate.

8 Claims, No Drawings

MANUFACTURE OF γ,δ-UNSATURATED KETONES

This invention relates to a process for the manufacture of γ,δ-unsaturated non-cyclic aliphatic ketones by reacting specific α,β-unsaturated ketones with vinylmagnesium halide in the presence of inorganic copper compounds at temperatures below 0° C.

It is generally known that alkylmagnesium halides add to ketones of the formula

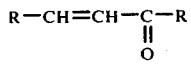

partially or predominantly in the 1,4-positions, but to ketones of formula I

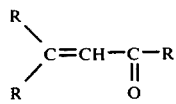

(R is a hydrocarbon radical) virtually exclusively in the 1,2-positions for steric reasons (see M. S. Kharash and O. Reinmuth in Grignard Reactions of Nonmetallic Substances, Prentice Hall Inc., New York, 1954, pp. 196 et seq.).

It is also known from J. Amer. Chem. Soc. 63 (1941), pp. 2308 et seq., that the reaction of pure methylmagnesium bromide with isophorone, i.e. a cycloaliphatic ketone of formula I, which usually proceeds with 1,2-addition, may be made to proceed with predominantly 1,4-addition if carried out in the presence of 1.0% molar of copper (I) chloride at temperatures of from 10° to 12° C.

However, in the corresponding reaction with mesityl oxide, i.e. a non-cyclic ketone of formula I, the 1,4-adduct (4,4-dimethylpentan-2-one) is formed only in small amounts (see Example 14).

According to J. Hooz et al (Can. J. Chem. 48 (1970), p. 1626) the copper-catalyzed Grignard reaction of ketones of formula I (for example mesityl oxide and isophorone) with vinylmagnesium bromide under the conditions given in J. Amer. Chem. Soc. 63 (1941) pp. 2308 et seq., leads to yields of the 1,4-adduct of only about 7 to 8% of theory. Hooz et al therefore recommend making γ,δ-unsaturated ketones by reacting mesityl oxide and isophorone with $(CH_2=CH)_2CuLiP(-n-C_4H_9)_3$.

It is further known to react 3-methyl-cyclohex-2-en-one with lithium propenyl cuprate to effect 1,4-addition giving 3-methyl-3-(1-propenyl)-cyclohex-2-en-one (Helv. chim. Acta 54 (1971) p. 1939). However, vinylation with the aid of lithium divinyl cuprate chelated by phosphines or propylenylation using lithium dipropenyl cuprate are extremely uneconomical processes, since there are required, per vinyl or propenyl group, 2 moles of lithium, 0.5 mole of CuI and, possibly, a further 0.5 mole of phosphine.

It is an object of the invention to provide a process by which γ,δ-unsaturated ketones may be produced in a less expensive manner by vinylation of ketones of formula I so as to make it possible to obtain γ,δ-unsaturated ketones on an industrial scale.

I have found, surprisingly, that, contrary to the results obtained by J. Hooz et al, the 1,4-adduct resulting from the reaction of non-cyclic aliphatic ketones of formula I with vinylmagnesium halides in the presence of simple inorganic copper compounds is obtained in very good yields if the reaction is carried out at temperatures below 0° C.

The invention thus relates to a process for the manufacture of γ,δ-unsaturated ketones of formula II

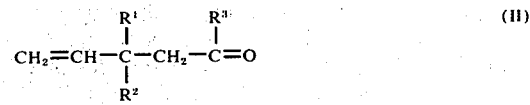

in which $R^1$ and $R^2$ denote alkyl of from 1 to 4 carbon atoms, preferably methyl, and $R^3$ denotes an aliphatic or cycloaliphatic hydrocarbon radical which contains up to 8 carbon atoms and which may have one or more C—C double bonds with the exception of the α,β-position to the carbonyl group and is preferably alkyl of from 1 to 8 carbon atoms, particularly methyl, by reacting a ketone of the general formula III

in which $R^1$ to $R^3$ have the meanings stated above, in the presence of inorganic copper compounds with a vinylmagnesium halide of formula (IV)

in which X denotes chlorine, bromine or iodine, which reaction is carried out at temperatures of from −80° to 0° C and preferably from −50° to −5° C.

A corresponding reaction of ketones of formula III with methyl-magnesium halides has not been observed (cf. Example 15).

Examples of suitable ketones of formula III are as follows:

2-methyl-2-penten-4-one, 3-methyl-3-hexen-5-one, 3-ethyl-3-hexen-5-one, 2-methyl-2-hexen-4-one, 2-methyl-2-hepten-4-one, 2-methyl-2-octen-4-one, 2-methyl-2-nonen-4-one, 2-methyl-2-decen-4-one, 2-methyl-2-undecen-4-one, 2-methyl-2-dodecen-4-one, 2,8-dimethyl-nona-2,7-dien-4-one, 2-methyl-2,6-heptadien-4-one, 3-methyl-3-hepten-5-one and 4-methyl-4-nonen-6-one.

Of particular significance is the reaction with 2-methyl-2-penten-4-one (mesityl oxide).

The ketones of formula III are obtained in a conventional and usually simple manner, for example by oxidation of the corresponding alcohols, by condensation of methyl ketones, by acylation of isobutene or by Meyer-Schuster rearrangement of acetylene alcohols.

Suitable vinylmagnesium halides are the chloride, bromide and iodide in the form of solutions thereof in ethers or hydrocarbons. I prefer the use as solution of vinylmagnesium chloride, particularly a solution thereof in tetrahydrofuran.

By inorganic copper compounds I mean copper compounds having no copper directly attached to a carbon atom, as against copper organic compounds such as $(CH_2=CH)_2CuLiP(n-C_4H_9)_3$ and lithium propenyl cuprate.

Suitable inorganic copper compounds are copper(I) salts and also copper(II) salts which may be converted under the conditions of the reaction to copper(I) salts by the Grignard reactant. Examples of copper(I) salts are: CuCl, CuBr, CuI, CuCN, Cu$_2$O, CuSCN and Cu$_2$SO$_4$ and copper(I) salts containing phosphines or CO as ligands, for example salts of the formulae (CuCOSX$_2$)$_2$ and (CuXPR$_3$)$_4$, in which X denotes Cl, Br or I and R is alkyl, aryl or alkoxyl. Examples of suitable copper(II) salts are: CuCl$_2$, CuBr$_2$, CuSO$_4$, Cu(OCOCH$_3$)$_2$, Cu(NO$_3$)$_2$, Cu(OH)$_2$, CuO, Cu(CNS)$_2$ and copper acetonyl acetonate.

I prefer to use the copper(I) salts, particularly CuCl, CuI and CuCN, since some of the copper(II) salts contain water of crystallization and their use thus involves increased consumption of Grignard compound or they are not readily soluble in the reaction mixture and the yields of the desired ketone of formula II are dependent on the solubility and reducibility of the copper(II) compound.

Suitable solvents for the reaction of the invention are aprotic solvents such as are usually employed in the preparation of Grignard compounds, for example aliphatic or aromatic hydrocarbons, e.g. pentane, hexane, benzene, toluene and ethers such as glycol dialkyl ether, diethyl ether, diisopropyl ether and tetrahydrofuran. I prefer to use tetrahydrofuran.

The process is carried out either by placing the vinylmagnesium halide solution in a vessel and adding the copper compound and then gradually adding the ketone of formula III, which may be dissolved in a solvent, whilst maintaining the reaction temperature specified by the invention, or by placing the ketone of formula III, which may be dissolved in a solvent, in a vessel and adding the copper compound and then gradually adding the vinyl magnesium halide solution whilst maintaining the reaction temperature specified by the invention. The reaction mixture is then maintained at said reaction temperature, with stirring, for the remainder of the reaction time. The former procedure is preferred. If desired, the process may be carried out continuously.

The reaction temperature is from $-80°$ to about $0°$ C and preferably from $-50°$ to $-5°$ C, the reaction time being from about 5 minutes to 5 hours depending on the ketone used and on the temperature at which the reaction is carried out.

The vinyl Grignard compound is used in an amount of 0.5 to 3.0 and preferably from 1.0 to 1.5 moles per mole of ketone of formula III.

The inorganic copper compound is generally used in catalytic amounts, i.e. in amounts of about 0.5 to 20% molar and in particular 1 to 10% molar, based on vinylmagnesium halide.

The process of the invention makes it possible to produce $\gamma,\delta$-unsaturated ketones of formula II in good yields and in a much more economical manner than hitherto, since the process requires only 1 mole of the cheap metal magnesium per vinyl group and only catalytic amounts of a simple copper compound, whereas the prior art processes either achieve only low yields or require 2 moles of lithium, 0.5 mole of CuI and, possibly, a further 0.5 mole of a phosphine per vinyl group.

The products of the process are valuable intermediates in the synthesis of a number of perfumes. For example, the 3,3-dimethyl-1-hexen-5-one which may be prepared from mesityl oxide and vinyl-magnesium chloride is an intermediate for lavandulyl compounds such as lavandulol and lavandulyl acetate.

One method of preparing lavandulyl acetate is, for example, to convert 3,3-dimethyl-1-hexen-5-one to 3,5,5-trimethyl-1,6-heptadien-3-ol by Grignard vinylation. This is then reacted with glacial acetic acid, acetic anhydride or acetyl halide in the presence of an acid catalyst to form the corresponding 3,5,5-trimethyl-1,5-heptadien-1-yl acetate which is then rearranged to the corresponding lavandulyl acetate by heating in an inert solvent to temperatures of from $150°$ to $250°$ C.

EXAMPLES 1 to 4

9.5 g (0.05 mole) of CuI are added at $-30°$ C to 365 ml (0.51 mole) of a 1.4M solution of vinylmagnesium chloride in tetrahydrofuran (THF), the mixture then being stirred for 15 minutes. At different temperatures, as listed in the Table below, 49 g (0.5 mole) of 2-methyl-2-penten-4-one in 100 ml of THF are added dropwise over 30 minutes and the reaction mixture is stirred for a further 30 minutes. After the addition of 50 ml of water, the solids are filtered off and the solution is concentrated. The crude product is distilled over a bridge and the distillate obtained at from $45°$ to $85°$ C at a pressure of 32 mm of Hg is examined gas chromatographically. The following Table lists the amount of distillate obtained and the composition thereof and also the yield of 3,3-dimethyl-1-hexen-5-one and the percentage conversion of 2-methyl-2-penten-4-one.

TABLE

| Ex. No. | Temperature (° C) | Amount of distillate (g) | (%) A | Composition of distillate B | C | Yield of B, Based on 100% conversion of A (%) | Conversion of A (%) |
| --- | --- | --- | --- | --- | --- | --- | --- |
| 1 | −50 | 55 | 12.6 | 85.3 | <0.1 | 85.7 | 87 |
| 2 | −30 | 56 | 12.6 | 84.5 | 0.18 | 87.7 | 86 |
| 3 | 0 | 44 | 12.5 | 67.8 | ≈0.5 | 53.3 | 89 |
| 4+ | +30 | 30 | 36 | 20 | 8.6 | 12.2 | 78 |

A = 2-methyl-2-penten-4-one
B = 3,3-dimethyl-1-hexen-5-one = 1,4 adduct
C = 2,4-dimethyl-hexa-2,5-dien-4-ol = 1,2 adduct
+= comparative example

EXAMPLE 5

(Comparative Example)

20 g (0.2 mole) of 2-methyl-2-penten-4-one in 50 ml of THF are added dropwise, at $0°$ C, to 150 ml of a 1.4M solution of vinylmagnesium chloride (0.21 mole) in THF over 30 minutes and the reaction mixture is stirred for a further 30 minutes. Following hydrolysis and filtering, the solvent is evaporated off and distillation is carried out over a bridge. 18 g of 2,4-dimethyl-hexa-2,5-dien-4-ol are distilled over at from 25° to 28° C at a pressure of 0.1 mm of Hg and this is found, by gas chromatographic methods, to contain less than 5% of 1,4 adduct. The yield of 2,4-dimethyl-hexa-2,5-dien-4-ol is 70% of theory.

EXAMPLE 6

9.5 g (0.05 mole) of CuI are added to 49 g (0.5 mole) of 2-methyl-2-penten-4-one in 100 ml of THF. 365 ml (0.51 mole) of 1.4M vinylmagnesium chloride in THF are then added dropwise, at −30° C, over 30 minutes, after which the reaction mixture is stirred for a further 30 minutes. The reaction mixture is worked up in a manner similar to that described in Example 1 to give 48 g of distillate having the following composition: 10% of 2-methyl-2-penten-4-one, 82% of 3,3-dimethyl-1-hexen-5-one and 2.7% of 2,4-dimethyl-hexa-2,5-dien-4-ol. This is equivalent to a yield of 69.4% of theory of 3,3-dimethyl-1-hexen-5-one, based on 100% conversion. The conversion of 2-methyl-2-penten-4-one is 90%.

EXAMPLE 7

Example 2 is repeated except that there are used, in place of 9.5 g of CuI, 20 g (0.0125 mole) of [CuI n—Bu$_3$P]$_4$ to give 54 g of distillate having the following composition: 21% of 2-methyl-2-penten-4-one, 76% of 3,3-dimethyl-1-hexen-5-one and 0.8% of 2,4-dimethyl-hexa-2,5-dien-4-ol. This is equivalent to a yield of 84.7% of theory of 3,3-dimethyl-1-hexen-5-one, based on 100% conversion. The conversion is 77%.

EXAMPLE 8

38 g (0.2 mole) of CuI are added, at −30° C, to 1,400 ml of a 1.45M solution of vinylmagnesium chloride (2.0 moles) in THF. The reaction mixture is then stirred for 15 minutes. 196 g (2.0 moles) of 2-methyl-2-penten-4-one in 200 ml of THF are then added dropwise over 30 minutes at −30° C, after which the mixture is stirred for 15 minutes. Fractional distillation of the crude product gives 19 g of 2-methyl-2-penten-4-one at 47°–56° C/50 mm and 202 g of 3,3-dimethyl-1-hexen-5-one at 64°–67° C/50 mm. This is equivalent to a conversion of the 2-methyl-2-penten-4-one of 90% and a yield of 3,3-dimethyl-1-hexen-5-one of 88.5% of theory, based on 100% conversion.

EXAMPLE 9

19 g (0.2 mole) of CuCl are added, at −30° C, to 1,320 ml of a 1.54M solution of vinylmagnesium chloride (2.0 moles) in THF, after which the reaction mixture is stirred for 15 minutes. 196 g (2.0 moles) of 2-methyl-2-penten-4-one in 200 ml of THF are then added dropwise, at −30° C, over 30 minutes, the reaction mixture then being stirred for a further 15 minutes. Fractional distillation gives 22 g (11.2%) of unreacted 2-methyl-2-penten-4-one and 212 g of 3,3-dimethyl-1-hexen-5-one. This is equivalent to a yield of 95% of theory, based on 100% conversion of the 2-methyl-2-penten-4-one. The conversion is 89%.

EXAMPLE 10

Example 9 is repeated except that there are used, in place of 19 g of CuCl, 18 g (0.2 mole) of CuCN to give 19 g of unreacted 2-methyl-2-penten-4-one and 198 g of 3,3-dimethyl-1-hexen-5-one. This is equivalent to a yield of 3,3-dimethyl-1-hexen-5-one of 87% of theory, based on 100% conversion. The conversion is 90.5%.

EXAMPLE 11

21 g (0.12 mole) of CuI are added over 5 minutes to 750 ml of a 1.5M solution of vinylmagnesium chloride (1.12 mole) in THF at −10° C. There are then added dropwise, at −10° C and over 15 minutes, 110 g (1.12 mole) of 2-methyl-2-penten-4-one in 100 ml of THF. The reaction mixture is then stirred for a further 2 minutes. Fractional distillation gives 12.4 g of 2-methyl-2-penten-4-one and 99.5 g of 3,3-dimethyl-1-hexen-5-one. This is equivalent to a yield of 79% of 3,3-dimethyl-1-hexen-5-one, based on 100% conversion. The conversion is 89%.

EXAMPLE 12

1.9 g (0.01 mole) of CuI are added, at −30° C, to 102 ml of a 1.45M solution of vinylmagnesium chloride (0.148 mole) in THF. There are then added, at −30° C and over 30 minutes, 13.8 g (0.09 mole) of 4-methyl-4-nonen-6-one and the mixture is stirred at −30° C for a further 30 minutes. After the addition of 50 ml of water, the solids are filtered off and the solution is concentrated. The crude product is distilled under high vacuum. 13.4 g of 4-methyl-4-vinyl-nonan-6-one are distilled over at 43°–45° C/0.1 mm. This is equivalent to a yield of 82.% of theory, based on 4-methyl-4-nonen-6-one converted.

EXAMPLE 13

19 g (0.1 mole) of CuI are added, at −30° C, to 770 ml of a 1.30M solution of vinylmagnesium bromide (1.0 mole) in THF, the reaction mixture then being stirred for 15 minutes. There are then added dropwise, at −30° C, 80 g (0.80 mole) of mesityl oxide in 100 ml of THF over 30 minutes, and the reaction mixture is stirred for a further 30 minutes at −30° C. Following hydrolysis and concentration as described in Example 1, the mixture is distilled under reduced pressure. There are obtained at 65° C to 100° C/100 mm 82 g of a product having the following composition as determined gas chromatographically:

2.9% of unreacted mesityl oxide (corresponding to a conversion of 97%)

89.5% of 3,3-dimethyl-1-hexen-5-one (corresponding to a yield of 73.5%, based on 100% conversion)

and less than 0.5% of 2,4-dimethyl-hexa-2,5-dien-4-ol.

EXAMPLE 14

(Comparative Example. Conversion similar to Kharash et al, J. Amer. Chem. Soc. 63 (1941), pp. 2308 et seq.)

0.81 g of CuCl (0.0082 mole) is added to 390 ml of a 2.09M clear solution of CH$_3$MgCl (0.817 mole) in diethyl ether in a 1 l round flask provided with a mercury-sealed stirrer, a thermometer, a dropping funnel and a reflux condenser. The reaction mixture is cooled to 5° C. A solution of 67.3 g (0.685 mole) of mesityl oxide in 135 ml of diethyl ether is then added over 1 hour, the reaction mixture being stirred and maintained at a temperature of 10°–12° C during said addition. The mixture is then heated for one hour and finally left to stand overnight. 380 g of ice and 49 g of glacial acetic acid are added to the reaction mixture and the separated ester layer is isolated. The aqueous phase is extracted with 75 ml of diethyl ether. The resulting ether extracts are combined and washed twice with sodium carbonate solution and twice with water and are then dried with anhydrous sodium carbonate and concentrated. Distillation of the reaction product under reduced pressure gives 48 g of a product boiling at 72°–103° C/100 mm and containing, according to gas chromatographic analysis, only 46% of the 1,4-adduct 4,4-dimethyl-pentan-2-one. This is equivalent to a yield of 32% of theory, based on mesityl oxide converted.

EXAMPLE 15

(Comparative Example)

9.5 g (0.03 mole) of CuI are added to 375 ml of a 1.33M solution of CH$_3$MgCl (0.5 mole) in THF at −30° C and the mixture is stirred for 15 minutes. A solution of 49 g (0.5 mole) of mesityl oxide in 100 ml of THF is then added dropwise over 30 minutes at −30° C and the reaction mixture is stirred for 30 minutes at −30° C. The mixture is worked up as in Example 2 to give 50 g of a distillate boiling at 55°–105° C/100 mm and containing, according to gas chromatographic analysis, the following components:

52.2% of unreacted mesityl oxide,
21.1% of 2,4-dimethyl-3-penten-2-ol (1,2-adduct),
less than 0.5% of 4,4-dimethyl-pentan-2-one (1,4-adduct),
25.4% of 2,4-dimethyl-1,3-pentadiene and
1.4% of unknown compounds.

I claim:

1. A process for the manufacture of γ,δ-unsaturated ketones of the general formula II

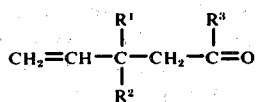    (II), in which R$^1$ and R$^2$ are alkyl of from 1 to 4 carbon atoms and R$^3$ is an aliphatic or cycloaliphatic hydrocarbon radical which contains up to 8 carbon atoms and which may contain one or more C—C double bonds in other than the α,β-position to the carbonyl group which comprises reacting a vinylmagnesium halide of formula IV CH$_2$=CH—Mg—X    (IV), in which X is Cl, Br or I, at −80° C to 0° C in an aprotic solvent with ketone of the general formula III

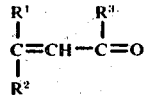    (III), in which R$^1$, R$^2$ and R$^3$ have the meanings stated above, in the presence of a catalytic amount of a copper compound selected from the group consisting of CuCl, CuBr, CuI, CuCN, Cu$_2$O, CuSCN, CU$_2$SO$_4$, CuCl$_2$ CuBr$_2$, CuSO$_4$, Cu(OCOCH$_3$)$_2$, Cu(NO$_3$)$_2$, Cu(OH)$_2$, CuO, Cu(CNS)$_2$, copper acetonyl acetonate, (CuCOX$_2$)$_2$ and (CuXPR$_3$)$_4$, in which X denotes Cl, Br or I and R is alkyl, aryl or alkoxy.

2. A process as claimed in claim 1, wherein the reaction is carried out in the presence of CuCl, CuBr, CuI, CuCN, Cu$_2$O, CuSCN or Cu$_2$SO$_4$ as said copper compound.

3. A process as claimed in claim 1, wherein the reaction is carried out in the presence of CuCl$_2$, CuBr$_2$, CuSO$_4$, Cu(OCOCH$_3$)$_2$, Cu(NO$_3$)$_2$, Cu(OH)$_2$, CuO, Cu(CNS)$_2$ or copper acetonyl acetonate as said copper compound.

4. A process as claimed in claim 1, wherein the reaction is carried out in the presence of a salt of the formulae (CuCOX$_2$)$_2$ or (CuXPR$_3$)$_4$, in which X denotes Cl, Br or I and R is alkyl, aryl or alkoxy, as said copper compound.

5. A process as claimed in claim 1, wherein the reaction is carried out in the presence of pentane, hexane, benzene, toluene, glycol dialkyl ether, diethyl ether, diisopropyl ether or tetrahydrofuran as said solvent.

6. A process as claimed in claim 1, wherein the reaction is carried out at −50° to −5° C.

7. A process as claimed in claim 1 wherein the amount of said copper compound present in the reaction mixture is 0.5 to 20 mol percent.

8. A process for the manufacture of 3,3-dimethyl-1-hexene-5-one which comprises reacting 2-methyl-2-pentene-4-one with a vinylmagnesium halide of formula (IV)

CH$_2$=CH—Mg—X    (IV), in which X is Cl, Br or I, at −80° to 0° C in the presence of a copper compound selected from the group consisting of CuCl, CuBr, CuI, CuCN, Cu$_2$O, CuSCN, Cu$_2$SO$_4$, CuCl$_2$, CuBr$_2$, CuSO$_4$, Cu(OCOCH$_3$)$_2$, Cu(NO$_3$)$_2$, Cu(OH)$_2$, CuO, Cu(CNS)$_2$, copper acetonyl acetonate, (CuCOX$_2$)$_2$ and (CuXPR$_3$)$_4$, in which X denotes Cl, Br or I and R is alkyl, aryl or alkoxy.

* * * * *